United States Patent [19]

Nemerson et al.

[11] Patent Number: 4,865,984
[45] Date of Patent: Sep. 12, 1989

[54] DYNAMIC CONTINUOUS FLOW ENZYME REACTOR

[75] Inventors: Yale Nemerson, Great Barrington, Mass.; Vincent Turitto, East Rockaway, N.Y.

[73] Assignee: Mount Sinai School of Medicine of the City University of New York, New York, N.Y.

[21] Appl. No.: 154,083

[22] Filed: Feb. 8, 1988

[51] Int. Cl.$^4$ .............................................. C12M 1/40
[52] U.S. Cl. ..................................... 435/288; 435/291
[58] Field of Search ............... 435/288, 310, 174, 284; 128/DIG. 22

[56] References Cited

U.S. PATENT DOCUMENTS

| | | | |
|---|---|---|---|
| 3,785,772 | 1/1974 | Coggeshall | 435/288 |
| 4,361,484 | 11/1982 | Larson et al. | 435/288 X |
| 4,452,682 | 6/1984 | Takata et al. | 204/403 |
| 4,604,182 | 8/1986 | Seago | 435/288 X |

OTHER PUBLICATIONS

Lottenberg et al., "Assay of Coagulation Proteases", Methods in Enzymology, 80: 341–361.
Bach et al., "Factor VII Binding to Tissue Factor in Reconsituted Phospholipid Vesicles: Induction of Cooperativity by Phosphatidylserine", Biochemistry, 25: 4007–4020 (1986).
Brian et al., "Allogenic Stimulation of Cytotoxic T Cells by Supported Planar Membranes", Proc. Natl. Acad. Sci. USA, 81: 6159–6163 (Oct. 1984).
Nemerson et al., "Progress in Hemostasis and Thrombosis", Spaet, T. H. edit., Grune & Stratton, New York, vol. 6, pp. 237–261 (1982).
Carson, Prog. Clin. Pathol., 9: 1–4 (1984).
Nemerson, Blood, vol. 71, No. 1, pp. 1–8 (1988).
Zur et al., "The Dual Role of Factor VII in Blood Coagulation", J. Biol. Chem., 257: 5623–5631 (1982).
Ragni et al., "Factor VII Deficiency", Amer. J. Hematol., 10: 79–88 (1981).

Primary Examiner—Larry Jones
Attorney, Agent, or Firm—Brumbaugh, Graves, Donohue & Raymond

[57] ABSTRACT

A dynamic continuous flow enzyme reactor and method for carrying out and analyzing phospholipid-dependent enzyme reactions are provided. The enzyme reactor is a tubular member preferably a capillary tube, coated on its inner surface with a planar phospholipid bilayer membrane, optionally and preferably containing an enzyme or enzyme cofactor. The reactor is connectable at one end to a means for delivering fluid flow reagents to the reactor and is connectable at a second end to a means for analyzing an effluent exiting from the reactor. Preferably the enzyme cofactor in the phospholipid membrane is purified tissue factor and the fluid reagents are inactive blood clotting factors which become activated upon interaction with the phospholipid membrane through a tissue factor-mediated reaction.

24 Claims, 3 Drawing Sheets

DYNAMIC CONTINUOUS FLOW ENZYME REACTOR

BACKGROUND OF THE INVENTION

The present invention relates to a dynamic continuous flow enzyme reactor and method which allow in vitro measurement of the rates of blood coagulation reactions and other dynamic enzymatic reactions which are dependent for activity on phospholipids in an environment closely approximating that found in the body.

The coagulation (clotting) system in man and animals is a major contributor to the maintenance of hemostasis and also to thrombus (blood clot) formation. Coagulation is essentially a cascade in which each clotting factor, which is normally present in the blood and other tissues as an inactive enzyme precursor, i.e., zymogen, is in sequence activated into a proteolytic enzyme that selectively attacks the next zymogen in the sequence, thereby converting it into an active enzyme. Amplification occurs at each step in the process so that a small initial stimulus can ultimately result in a significant amount of fibrin clot.

The clotting cascade begins as two separate pathways that ultimately converge. One pathway is "intrinsic" to the blood and the other one is termed "extrinsic" because it is triggered by clotting factors not normally present in blood. The intrinsic pathway plays a major role in hemostasis following injury. The extrinsic pathway can become activated in a variety of pathologic situations, e.g., diffuse endothelial damage, advanced cancer, endotoxemia, and pregnancy complications.

There is now considerable evidence that coagulation is started in the body when factor VII, a vitamin K-dependent plasma clotting factor protein and tissue factor, a cellbound protein not normally associated with blood cells, interact. (See e.g. Nemerson, Blood 71:1-8, 1988 for a review). This interaction results in an activated complex which has enzymatic activity and initiates clotting by converting two other proteins, i.e., factor X and factor IX, to their active, enzymatic forms, factor $X_a$ and factor $IX_a$, respectively. (In accord with common practice, precursor, i.e., the zymogen, forms of the active blood clotting factors are denoted by a Roman numeral, and the active forms are indicated by a subscripted "a", e.g. factor X for zymogen and factor $X_a$ for activated factor.)

Tissue factor is a procoagulant protein present on the surface of virtually all cells, not normally in direct contact with blood. However, tissue factor is inducible in endothelial cells and monocytes upon stimulation with various pharmacologic mediators, e.g. tumor necrosis factor, interleukin-1 and endotoxin. The extrinsic coagulation pathway is triggered by tissue factor which complexes with and activates factor VII, a vitamin K-dependent serine protease zymogen. The activation of factor VII by tissue factor occurs in the presence of calcium ions and is believed to result from a conformational change in factor VII. See, e.g., Nemerson et al. (1982) in Progress in Hemostasis and Thrombosis, Spaet, T. H. edit., Grune & Stratton, New York, vol. 6, pp. 237-261; Carson (1984) Prog. Clin. Pathol. 9:1-14. Conversion of the factor VII zymogen to the factor $VII_a$ active enzyme is accomplished by cleavage of an arg-ile peptide bond in the zymogen resulting in factor $VII_a$ which has a light chain containing the Gla region and a heavy chain that contains the enzyme active site.

If the zymogen factor VII had procoagulant activity, then the initiation of coagulation could simply follow upon the breaking of a physical barrier that normally separates factor VII from tissue factor. Thus, for hemostatis to occur, the injury itself may be sufficient to initiate coagulation. The determination that a zymogen has a small amount of activity relative to its derivative enzyme is fraught with difficulty because an active zymogen would have the same activity as an inert zymogen contaminated with a trace amount of an enzyme. In most instances, this problem is approached simply by treating the zymogen with an active site-directed enzyme inhibitor such as diisopropylfluorophosphate (DFP) or an appropriate chloromethylketone, thereby inhibiting the contaminating enzyme. Because zymogens usually are almost inert, this results in a total loss of measurable activity. However, the factor VII zymogen is itself readily inhibited by DFP, thus obviating this straightforward approach. Indeed, the reactivity of factor VII toward DFP is so great that by itself, it suggests extraordinary activity of the factor VII zymogen.

The DFP inhibition studies using bovine factors VII and $VII_a$, showed that factor VII qualitatively has the same enzymatic activity as factor $VII_a$ although the factor VII zymogen contains slightly less than 1% of the activity of factor $VII_a$. DFP has also been shown to inhibit human factor VII, the rate being one third of that for the inhibition of factor VIIa, which is about the same ratio observed when bovine proteins were used. See, e.g. Nemerson, Blood 71:1-8, 1988 and Zur et al., J. Biol. Chem. 257:5623-5631, 1982.

Experiments support the notion that coagulation can be initiated simply by the physical complexation of tissue factor and factor VII. Further evidence for this concept is derived from the observation that bovine factors VII and $VII_a$ bind to tissue factor with essentially the same dissociation constants. When monocytes were used as a source of human tissue factor, the same phenomenon was observed for human factors VII and $VII_a$. Accordingly, one need not postulate a proteolytic initiation of coagulation, thereby avoiding the problem of an infinite regression of proteolytic events. This degree of activity of the zymogen is unusual in general and appears to be unique in the clotting system. The activity of factor VII or, indeed factor $VII_a$ is compatible with a quiescent coagulation system because in the absence of tissue factor it cannot trigger coagulation.

Owing to its intrinsic reactivity, factor VII is distinguished from all other known clotting zymogens. Thus, because the factor VII zymogen has enzymatic activity, when both the zymogen and active enzyme are referred to without distinguishing between the two species, the designation of factor VII(a) is used.

Tissue factor is likewise unique among the cofactors because, in contrast to the clotting factors V and VIII and other cofactors in the clotting cascade, the mature tissue factor protein apparently requires no further processing for its activity. These observations taken together suggest that the only requirement for the initiation of coagulation by tissue factor is its physical complexation with factor VII.

Tissue factor, which is a membrane-bound glycoprotein associated with phospholipids, is not normally present in the circulation. When blood vessels are disrupted, however, factor VII, which is a plasma coagulation factor, can complex with tissue factor, thereby forming a catalytically-active species which activates both factor IX (plasma thromboplastin component) a component of the intrinsic pathway to form factor $IX_a$ and factor X (Stuart factor), which is involved in both the extrinsic and intrinsic pathways of coagulation, to yield factor $X_a$. Tissue factor also has important clinical use as a diagnostic reagent to monitor and study clotting.

Factor VII is present in trace amounts in the plasma (ca. 10 nM). The severe bleeding seen in individuals who are markedly deficient in factor VII demonstrates the physiologic importance of this protein. Deficiencies of factor VII are rare, but recent evidence suggests that some 16% of affected patients have cerebral hemorrhages usually resulting in death. Ragni et al., Factor VII Deficiency, Amer. J. Hematol., 10:79–88 (1981). On the other hand, patients with as little as 5% of the normal levels of factor VII sometimes have little or no hemorrhagic symptoms. For any given factor VII level, however, there is considerable clinical variability.

A variety of disorders, e.g. cancer and cardiovascular disease, are associated with increases in blood clot formation in the blood vessels. A main treatment for cardiovascular disease involves the use of anticoagulants, e.g. warfarin and related drugs, which interfere with the synthesis of vitamin K-dependent clotting factors (e.g., factors II, VII, IX and X). There are many studies which indicate that this treatment decreases the incidence of venous thromboembolism, pulmonary embolism and myocardial infarction (heart attacks). However, warfarin therapy is also associated with a rather high incidence of hemorrhage, which is sometimes fatal.

The standard way in which the dosage of the warfarin-type anticoagulants is monitored is by using the Quick one-stage prothrombin time. In this test, which is performed under static conditions, a sample of the patients blood plasma is warmed to 37° C. A suspension of tissue thromboplastin (crude tissue factor) is then added to the plasma sample together with calcium ions and the clotting time is determined. Normal clotting time is $12+/-0.5$ seconds. The therapeutic range of the anticoagulant is a blood concentration of the drug which provides a clotting time which ranges between 1.2 and 1.5 times the normal value. This narrow range imposes on clinical laboratories a precision which is frequently not attainable. These inaccuracies are believed to be responsible for some of the hemorrhagic side effects of the anticoagulant drugs.

Factor VII can be measured in a similar manner. Dilutions of the patient's plasma are added to normal plasma and the one-stage prothrombin time test is performed. The amount of factor VII present in the test sample is estimated by comparing the clotting times of the test samples with those obtained from dilutions of normal plasma. Indeed, to date all tests of the coagulation system have been based on the determination of clotting times of various plasmas, but always in a test tube under static conditions. However, because blood coagulation in vivo always occurs in a moving stream, the effects of flow on the enzymatic reactions cannot be properly evaluated in a static system.

It has now been found that the specific blood clotting enzymatic reactions can be more specifically performed in a dynamic fashion by passing various blood clotting zymogens together with calcium ions at a defined flow rate through a tubular housing member which is coated on its inner surface with a planar phospholipid bilayer membrane. Optionally and preferably the planar membrane has purified tissue factor incorporated therein. The reagents passed through the housing include either factor VII or factor $VII_a$, which complexes with the tissue factor to form an enzymatically active species, together with factor IX or factor X which are the substrates for the tissue factor—factor VII complex. The rates of factor $IX_a$ or factor $X_a$ production can be readily analyzed by any suitable assay for these factors. The dynamic reaction allows for more specific analysis of the production of activated factors than can be obtained by current static methods.

Furthermore, passage of a plasma sample, e.g. from a patient, through such a phospholipid membrane-coated device under defined flow rates and other conditions of the invention allows the measurement of specific enzymatic products produced by interaction of the plasma sample with the tissue factor-containing phospholipid membrane and can provide valuable information on deficiencies of specific clotting factors or a more sensitive monitoring of proper anticoagulation parameters in patients than was obtainable by prior methods.

The enzyme reactor of the invention may also be used for carrying out and analyzing other phospholipid-dependent enzymatic reactions other than blood clotting reactions. Such reactions involve flowing various inactive enzyme reaction components in the reagent solution through a phospholipid bilayer membrane-coated tubular housing. The inactive enzyme components in the reagent solution become enzymatically active by interaction with the phospholipid membrane on the inner surface of the housing and the products of the reaction can be analyzed in the effluent solution.

SUMMARY OF THE INVENTION

In accordance with the present invention, a dynamic continuous flow enzyme reactor is provided which allows in vitro measurement of the rates of blood coagulation reactions and other phospholipid-dependent enzymatic reactions in an environment closely approximating that found in the body. Also in accordance with the present invention, a method of measuring the rates of activation of various clotting factors is provided, in particular activation of factor X to factor $X_a$ and factor IX to factor $IX_a$, both via factor VII or factor $VII_a$, as well as a method of measuring the rate of thrombin production.

DETAILED DESCRIPTION OF THE INVENTION

Figure 1:
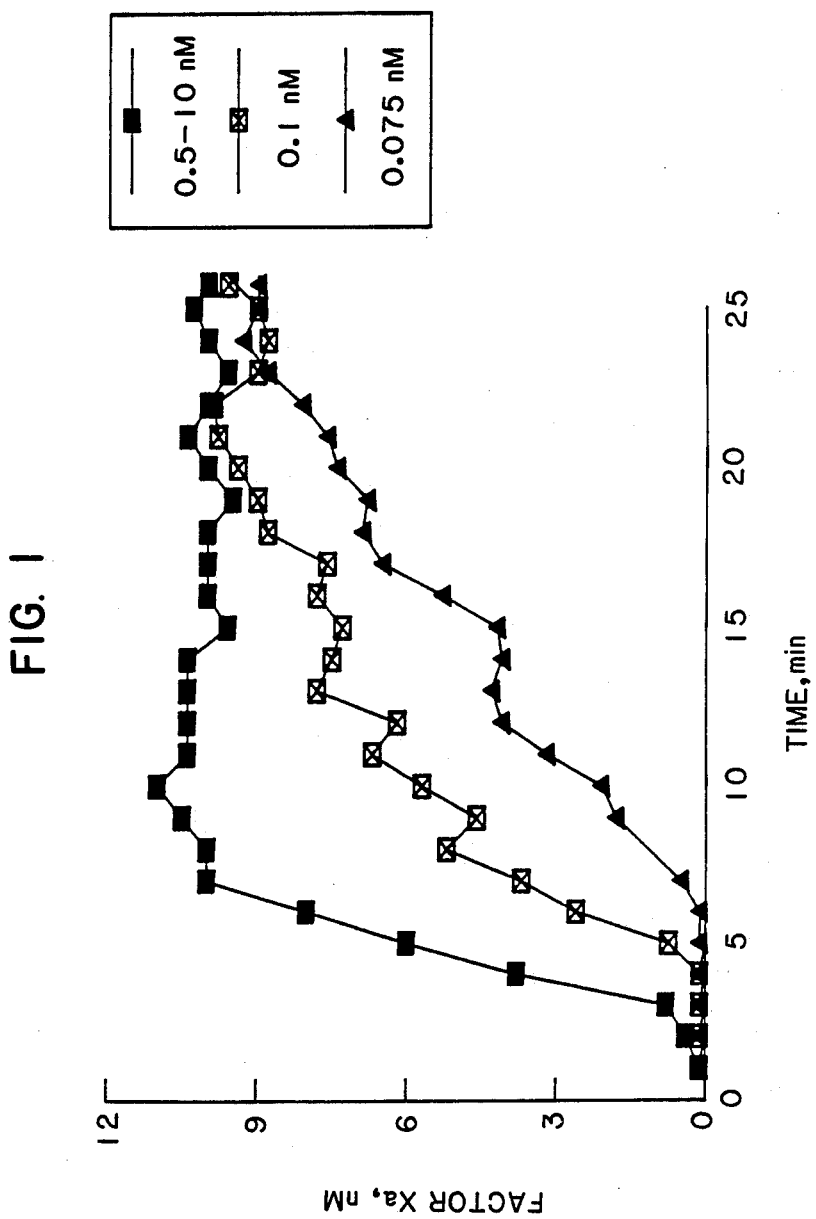
FIG. 1 illustrates the activation of factor X by factor $VII_a$ and tissue factor according to one embodiment of the present invention.

The present invention relates to a dynamic continuous flow enzyme reactor, which comprises a tubular housing coated on its inside surface with a lipid membrane comprising a planar phospholipid bilayer optionally and preferably containing an enzyme or an enzyme cofactor. The tubular housing has one end which is connectable to a means for delivering specific fluid reagents thereto and connectable at a second opening to a means for collecting and analyzing an effluent fluid therefrom. Preferably the tubular housing is a capillary tube open or openable at both ends.

Various purified clotting factors or zymogens or, alternatively plasma may be pumped through the enzyme reactor along with calcium ions and allowed to react with the enzyme or cofactor in the phospholipid membrane. By controlling the flow rates of these factors as they enter the reactor and measuring the concentrations of products in the effluent fluid leaving the reactor, the activation rates of the various zymogens of the blood clotting cascade to active products can be estimated and the effect of flow on product formation can be determined. In addition, the time to reach a steady state production level of any of the activated species can also be calculated.

In accordance with the preferred embodiment of the invention, the phospholipid bilayer contains purified tissue factor which is the enzyme cofactor which initiates activation of blood clotting factors. Clotting factors which are pumped through the reactor are factor VII or factor $VII_a$ together with factor IX or factor X. The clotting factors are pumped through the phospholipid membrane-coated capillary tube with calcium ions and allowed to flow over the tissue factor-containing phospholipid bilayer membrane on the inner surface of the tube. When the tissue factor in the membrane contacts factor VII or factor $VII_a$ in the flow material, an enzymatically active complex is formed inside the capillary tube. This enzymatically active complex in turn activates factor IX into factor $IX_a$ or factor X into factor $X_a$ in the flow material. By controlling the flow rates and concentrations of factor IX or factor X and factor VII or factor $VII_a$ at the inlet of the reactor and monitoring the concentrations of factor $IX_a$ or factor $X_a$ in the effluent from the reactor, the activation rates of factor IX to factor $IX_a$ or factor X to factor $X_a$ can be calculated and the effects of flow thereon can be determined. In addition, the time to reach steady state production of factor $IX_a$ or factor $X_a$ for various concentrations of factor VII or $VII_a$ can also be calculated.

Factor VII may be substituted for factor $VII_a$ and vice-versa, since, as discussed above, the zymogen factor VII qualitatively has the same procoagulant activity as its active enzyme derivative factor $VII_a$, albeit the activity of the zymogen is only about 1% of the active enzyme. Zur et al., J. Biol. Chem. 257: 5623-5631 (1982); Nemerson, Blood 71: 1-8 (1988). Factor VII thus can be employed as a starting material in the present enzyme reactor without preprocessing into factor $VII_a$.

In accordance with another embodiment of the present invention, a mixture of purified factor VII or factor $VII_a$, together with the purified clotting factors factor V, factor VIII, factor IX and factor X can be introduced into the membrane-coated capillary tube along with prothrombin. The rate of thrombin production, factor $IX_a$ production, or factor $X_a$ production can then be measured, and the effect of various concentrations of each of the clotting factors on thrombin, factor $IX_a$, or factor $X_a$ production can be monitored.

In accordance with still another embodiment of the present invention, plasma may be introduced into the phospholipid membrane-coated enzyme reactor at a constant flow rate, in order to initiate activation of clotting factors by interaction with the tissue factor in the phospholipid membrane. Production of selected factors such as $IX_a$, $X_a$, or thrombin can then be measured. This embodiment allows a more specific evaluation of clot formation than can be obtained by the static measurement of prothrombin times and is applicable to evaluate patients with clotting deficiencies or subjects on anti-coagulant therapy.

The capillary tube of the continuous flow enzyme reactor may be of varying dimensions, and may have an internal diameter between about 0.10-1.10 mm and a length of about 1-15 cm. At low wall shear rates, (ca 20 $sec^{-1}$) product formation is proportional to the size of the capillary tube according to the equation $(L/Q)^{\frac{1}{3}}$ where L is tube length and Q is the flow rate through the reactor, which is indicative of a diffusion controlled reaction. At high shear rates (greater than 100 $sec^{-1}$) it is believed that diffusion becomes less important and enzyme kinetics predominate.

The capillary tube is prepared by first immersing it in a boiling detergent solution, for example Sparkleen TM, and then rinsing it in distilled deionized water in an ultrasonic bath. It is then dried at 120° C. and filled with a suspension of lipid vesicles containing tissue factor. The capillary tube is then flushed with a buffer solution of 0.01M N-2-hydroxyethyl piperazine-N'-2-ethane sulfonic acid (HEPES) with 0.14M NaCl and 1 mg/ml bovine serum albumin (BSA) in which the pH is adjusted to 7.5 with HCl. The filled capillary tube is finally stored at room temperature in the buffer solution to prevent exposure of the membrane to air.

The suspension of lipid vesicles containing purified tissue factor is preferably prepared according to the method described in Bach et al., "Factor VII Binding to Tissue Factor in Reconstituted Phospholipid Vesicles: Induction of Cooperativity by Phosphatidylserine", Biochemistry 25:4007 (1986), which involves incorporation of tissue factor into phospholipid vesicles in the presence of a large excess, e.g. a 15-fold molar excess, of the dialyzable nonionic detergent octyl glucoside. Removal of the detergent by dialysis results in the spontaneous incorporation of purified tissue factor in large phospholipid vesicles. The vesicles are prepared from a mixture of phosphatidylserine or other acidic phospholipids and phosphatidylcholine. Preferably a mixture of 0-40% phosphatidylserine (PS) and 60-100% phosphatidylcholine (PC) is complexed with tissue factor at a ratio of approximately 1-10 moles tissue factor to 100,000 moles phospholipid.

Purified tissue factor may be prepared by known techniques from bovine brain or human brain or placenta (See e.g. Spicer et al., Proc. Natl. Acad. Sci. 84:5148-5152, 1987) or produced by recombinant DNA cloning techniques as provided in U.S. patent application Ser. No. 062,166 of Nemerson et al., filed June 12, 1987.

Figure 2:
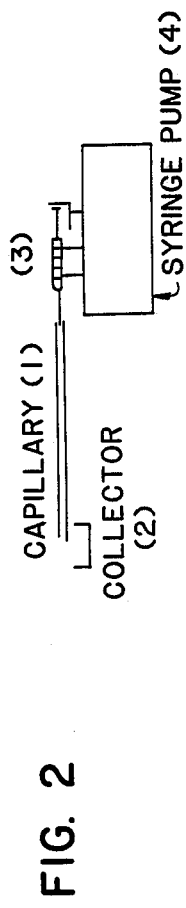
FIG. 2 is a diagram of the continuous flow enzyme reactor of the present invention.
Figure 3:
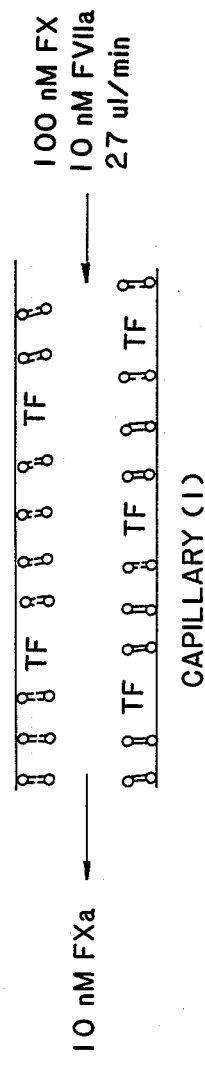
FIG. 3 is a longitudinal view of the continuous flow enzyme reactor of the present invention.
Figure 4:
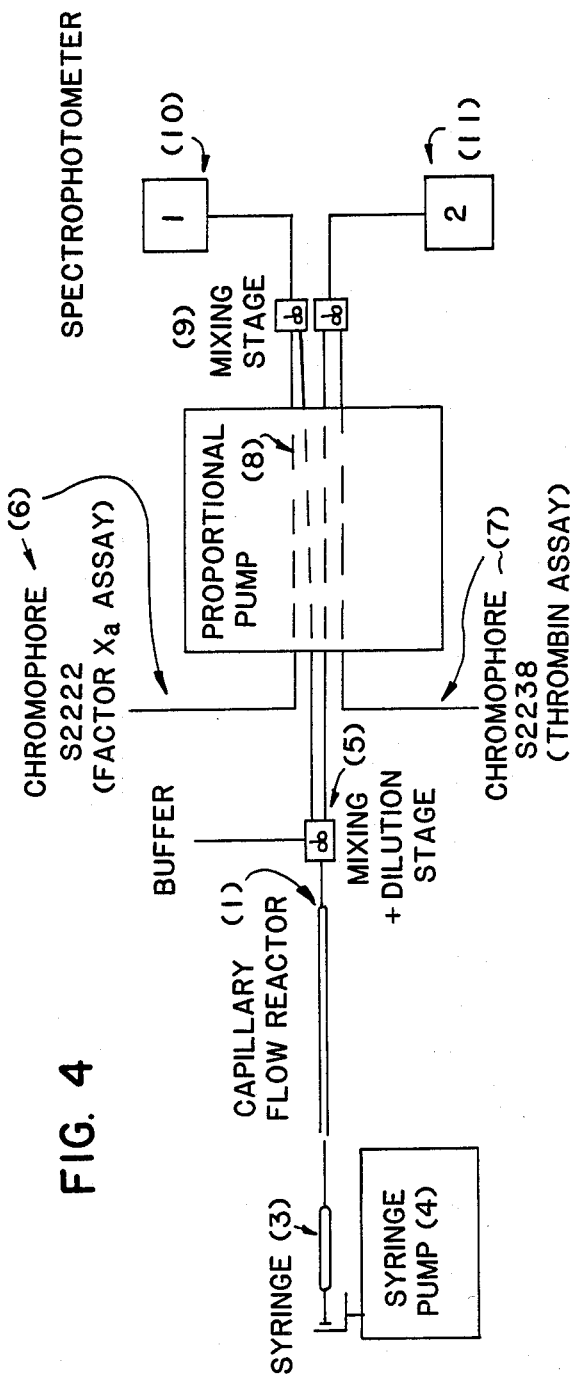
FIG. 4 is a diagram of the continuous flow enzyme reaction of the present invention connected to a means for pumping reagents into the reactor and a means for analyzing the effluent from the reaction for both thrombin and factor $X_a$.

Referring to FIGS. 2 and 4, when the enzyme reactor is to be used, the capillary tube (1) is removed from the storage buffer and is connected to a syringe (3) containing a solution of calcium ions and either factor VII or factor $VII_a$ and one or more of purified clotting factors including factor V, factor VIII, factor IX, factor X and prothrombin. These purified factors may be obtained by known protein isolation techniques or produced by recombinant DNA cloning techniques. Using a pump (4) the solution is passed through the capillary tube (1) at a constant rate and the various clotting factors are allowed to react with the tissue factor—containing planar phospholipid membrane. The effluent material containing activated enzyme products is then collected in the collector (2) at the exiting end of the capillary tube (1) and analyzed.

The production rates of selected enzymes are then measured. One method of measuring the production rates of factor $IX_a$ or factor $X_a$ is to use tritium-labelled factor IX or factor X as a starting material, and then measure the amount of acid soluble tritium produced in the effluent of the capillary tube. In addition, standard radioassays or fluorescent (fluorogenic) assay techniques can be used to analyze the products of enzyme reactions taking place within the reactor of the present invention. When using a fluorescent assay, the interaction of the various chemical components is followed by measuring the fluorescence of the effluent of the capillary tube as a function of time.

Another method of measuring the production rate of a given enzyme is to add a chromogenic substrate specific for an enzyme product to the effluent of the enzyme reactor, and then to direct the stream through a continuous flow photometer. For example as shown in FIG. 4, when the production rate of factor $X_a$ is to be measured, chromogenic substrate S2222 ® (6) (Lottenberg et al., Meth. Enzymol. 80:341–361, 1981) is added to the effluent before passing through the photometer. Then the concentration of factor $X_a$ formed in the enzyme reactor can be measured by changes in optical absorbance at 405 nm. Or for example, when the production rate of thrombin is to be measured, chomogenic substrate S2238 ® (7) (Lottenberg et al., Meth. Enzymol. 80:341–361, 1981) is added to the effluent of the enzyme reactor before it enters the photometer. If more than one enzyme production rate is to be measured simultaneously, the exit stream of the enzyme reactor can be split and different chromogenic substrates can be added to each stream and measured separately for optical absorbance. A proportional pump (8) is used to send the stream to a mixing stage (9), after which the separate streams are sent to spectrophotometers (10) and (11).

Using the concentration levels measured for one or more enzyme products, the time to reach a steady state level of production for each of these products can be calculated. For purposes of analysis, the time to reach one-half the steady state production ($T_{\frac{1}{2}}$) of a given product may also be measured, which provides for easier comparison of data. This new parameter, i.e., time to reach steady state production, which can now be obtained using the continuous flow enzyme reactor of the present invention, allows for enhanced analysis of blood clotting mechanisms. In contrast, conventional static clotting assays cannot yield information about steady state conditions, nor can they be used to evaluate the effects of flow rate on time to reach steady state.

The enzyme reactor of the present invention is stable to wall shear rates of at least 3000 sec$^{-1}$, which is comparable to the maximum average wall shear rates in the vasculature of the human body, i.e., about 2000 sec$^{-1}$ to 5000 sec$^{-1}$.

The following non-limiting examples are intended to further illustrate the present invention.

EXAMPLE 1

Phospholipid vesicles containing purified tissue factor obtained by recombinant DNA cloning techniques as described in U.S. patent application Ser. No. 062,166 or by known protein isolation techniques from bovine brain or human brain or placenta powders as described by Spicer et al., Proc. Natl. Acad. Sci. 84:5148–5152, 1987 were prepared in the following manner. PS and PC in CHCl$_3$ were combined in molar ratios varying from 0:100 (PS:PC) to 40:60 (PS:PC) and dried to a thin film on the wall of a borosilicate glass tube under a stream of N$_2$ and then in vacuo for 2 hours. A 15-fold molar excess of octyl glucoside (200 mM) in 0.1M NaCl and 0.05M Tris, pH at 7.5 (TBS) was then added, and the mixture was incubated at room temperature with occasional vortexing until it was completely clear.

Purified tissue factor in TBS containing 0.1% Triton ® X-100 was added to the phospholipid-octyl glucoside preparation, giving a final solution in which the concentration of Triton ® X-100 was <0.02% and the tissue factor: phospholipid: octyl glucoside molar ratio was 110:100,000: 1,500,000.

Tracer amounts of [$^{14}$C] PC and $^3$H-tissue factor were added for precise quantification of protein and phospholipid in the final material. The ratio of $^3$H counts to $^{14}$C counts was approximately 10–100 to 1 (depending on tissue factor concentration). Aliquots were taken for liquid scintillation counting, and the remainder was dialyzed against 3×1 liter of TBS at room temperature for 72–96 hours, after which the material was gel filtered at room temperature in TBS on a column of Sepharose ® CL-2B (1.5×55 cm). The recovery of $^3$H-tissue factor and $^{14}$C-phospholipid was determined by liquid scintillation counting. The resulting suspension consisted of 2 mM PS/PC lipid vesicles and 20–200 nM tissue factor.

Standard glass capillaries were prepared by first immersing them in a boiling detergent solution of 1 g Sparkleen TM /500 ml distilled/deionized water for 30 minutes and rinsing them three times for 5 minutes with distilled/deionized water in an ultrasonic bath for a total of 15 minutes. The capillary tubes were then dried at 120° C. for 30 minutes, and were filled with the prepared suspension of PS/PC lipid vesicles containing tissue factor. After 10 minutes the tubes were flushed with HEPES/albumin buffer (0.01M HEPES, 0.14 NaCl, 1 mg/ml BSA, with the pH adjusted to 7.5 using HCl) and stored immersed in the buffer to prevent contact of the lipid membrane with air.

EXAMPLE 2

Capillary tubes (I.D.=0.56 mm, L=75 mm) as prepared and coated according to the method described in Example 1 were connected to a syringe containing various solutions of factor VII$_a$, 100 nM of tritium-labelled factor X and 5 mM CaCl$_2$. Using a precision pump, the solutions were passed through the tubes at a constant flow rate of 27.1 μl/min. the tubes were then analyzed for factor $X_a$ production and concentration by measuring the amount of acid soluble tritium produced. The results at steady-state are shown in Table 1.

TABLE 1

| Capillary Tube | | Flow Rate into Enzyme Reactor μl/min | CONCENTRATIONS ENTERING CAPILLARY TUBE | | Steady State Concentration |
|---|---|---|---|---|---|
| I.D. mm | L mm | | Factor VII$_a$ nM | Factor X nM | Factor X$_a$ nM |
| 0.56 | 75 | 27.1 | 1 | 100 | 8.4 |
| 0.56 | 75 | 27.1 | 0.5 | 100 | 9.8 |
| 0.56 | 75 | 27.1 | 0.1 | 100 | 8.8 |
| 0.56 | 75 | 27.1 | 0.075 | 100 | 8.4 |

As can be seen, the concentration of factor X$_a$ formed was independent of the factor VII$_a$ concentration at steady-state. However, FIG. 1 illustrates the amount of factor X$_a$ produced over time for the above four concentrations of factor VII$_a$. It was found that the time to reach the steady state level of factor X$_a$ varied inversely with factor VII$_a$ concentrations. In addition, factor VII was utilized under the same conditions and gave similar results, that is, as the concentration of factor VII decreased, time to reach steady state increased. For a factor VII concentration of 0.1 nM, the steady state concentration of factor X$_a$ was 10.6 nM.

Since the approach to steady state production of factor X$_a$ was gradual, T$_{\frac{1}{2}}$ of factor X$_a$ was calculated. In FIG. 1, it is shown T$_{\frac{1}{2}}$ was similar from concentrations of 0.5-10 nM of factor VII$_a$, namely approximately 4 minutes. These factor VII$_a$ levels corresponded to 5-100% of normal factor VII levels in the human body, while severe bleeding usually occurs when the factor VII level in the body is less than 5%. As shown in FIG. 1, as levels of factor VII$_a$ dropped to 0.1 nM (1% of normal) and 0.075 nM (0.75% of normal), T$_{\frac{1}{2}}$ increased markedly. The wall shear rates developed in this Example approximated those in the human venous system, e.g. about 20-40 sec$^{-1}$.

EXAMPLE 3

The same experimental conditions were carried out as in Example 2, except the dimensions of the capillary tube and the flow rate were varied. The results for an internal diameter of the capillary tube equal to 0.33 mm and length equal to 125 mm are given in Table 2.

TABLE 2

| Capillary Tube | | Flow Rate into Enzyme Reactor μl/min | CONCENTRATIONS ENTERING CAPILLARY TUBE | | Steady State Concentration |
|---|---|---|---|---|---|
| I.D. mm | L mm | | Factor VII$_a$ nM | Factor X nM | Factor X$_a$ nM |
| 0.33 | 125 | 200 | 1 | 200 | 3.20 |
| 0.33 | 125 | 400 | 1 | 200 | 2.40 |

At the lower flow rate (200 μl/min), the calculated wall shear rate was 856 sec$^{-1}$, which is intermediate between the average wall shear rates obtained in small arteries and in microcirculation; at 400 μl/min, the obtained wall shear rate was 1712 sec$^{-1}$, similar to microcirculatory rates. Thus, the enzyme reactor was clearly stable to shear rates comparable to the physiological range. Accordingly, the effect of various abnormalities of the coagulation system can be evaluated under flow conditions ranging from those in the venous system to those in microcirculation.

It was found that capillary tubes with internal diameters ranging from about 0.10 to 1.10 mm and tube lengths ranging from about 1.0-15 cm were acceptable. Changes in tube diameter were found to alter the amount of products produced, but not the basic mechanism of the invention.

The above Examples demonstrate the type of data that can be obtained using the continuous flow enzyme reactor of the present invention, which is not available using known static techniques. The foregoing is not intended to limit the scope of the invention, since the presently claimed enzyme reactor can be used to measure thrombin production rates, production of clotting factors in whole plasma and a variety of other phospholipid dependent enzyme reactions.

We claim:

1. A dynamic continuous flow enzyme reactor for carrying out and analyzing phospholipid-dependent enzymatic reactions which comprises a tubular housing coated on its inner surface with a planar phospholipid bilayer membrane, the housing being connectable at one opening to a means for delivering fluid flow reagents thereto and connectable at a second opening to a means for collecting and analyzing an effluent fluid therefrom.

2. The enzyme reactor of claim 1 wherein the housing is a capillary tube.

3. The enzyme reactor of claim 1 wherein the housing is a capillary tube having an inner diameter of about 0.1 to 1.1 mm and a length of about 1.0 to 15 cm.

4. The enzyme reactor of claim 1 wherein the phospholipid membrane comprises at least one additional component selected from the group consisting of enzymes and enzyme cofactors.

5. The enzyme reactor of claim 4 wherein the cofactor is tissue factor.

6. The enzyme reactor of claim 5 wherein the phospholipid membrane contains tissue factor in a ratio of approximately 1-10 moles of tissue factor per 100,000 moles of phospholipid.

7. The enzyme reactor of claim 1 wherein the phospholipid membrane comprises neutral and acidic phospholipids.

8. The enzyme reactor of claim 1 wherein the phospholipid membrane comprises phosphatidylcholine and phosphatidylserine.

9. The enzyme reactor of claim 1 wherein the phospholipid membrane comprises a mixture of 60-100% phosphatidylcholine and 0-40% phosphatidylserine.

10. The enzyme reactor of claim 1 wherein the phospholipid membrane comprises a mixture of 70% phosphatidylcholine and 30% phosphatidylserine.

11. A method for continuously carrying out and measuring dynamic enzyme reactions comprising:
(a) delivering reagents for performing an enzymatic reaction at a defined flow rate to an inlet in a dynamic continuous enzyme flow reactor comprising a tubular housing which is coated on its inner surface with a planar phospholipid bilayer membrane, wherein the reagents and membrane components are separately inactive for performing the enzymatic reaction, but together yield an enzymatically active system;

(b) pumping the reagents through the enzyme reactor at a constant and defined flow rate so that an enzyme reaction mediated by contact of the reagents with the phospholipid membrane takes place in the enzyme reactor;

(c) collecting a product of the enzyme reaction in an effluent from an exit in the enzyme reactor; and (d) measuring the amount of product formed during the enzyme reaction by means of a suitable assay.

12. Method according to claim 11 wherein the phospholipid membrane further comprises at least one additional component selected from the group consisting of enzymes and enzyme cofactors.

13. Method according to claim 12 wherein the cofactor is tissue factor.

14. Method according to claim 13 wherein the reagents comprise blood clotting factors and calcium ions.

15. Method according to claim 14 wherein the blood clotting factors comprise a blood clotting factor selected from the group consisting of factor VII and factor $VII_a$, together with at least one factor selected from the group consisting of factor IX, factor X, factor V, factor VIII, prothrombin and whole plasma.

16. Method according to claim 14 wherein the blood clotting factors are factor VII and factor IX.

17. Method according to claim 14 wherein the blood clotting factors are factor $VII_a$ and factor IX.

18. Method according to claim 14 wherein the blood clotting factors are factor VII and factor X.

19. Method according to claim 14 wherein the blood clotting factors are factor $VII_a$ and factor X.

20. Method according to claim 14 wherein the blood clotting factors are factor VII, factor X, factor V and prothrombin.

21. Method according to claim 14 wherein the blood clotting factors are factor $VII_a$, factor X, factor V and prothrombin.

22. Method according to claim 11 wherein the assay for measuring the amount of product is selected from the group consisting of radioassays, chromogenic assays and fluorogenic assays.

23. Method according to claim 11 further comprising adding a chromogenic or fluorogenic substrate specific for the product of the reaction to the effluent before measuring the amount of product formed.

24. Method according to claim 11 further comprising splitting the product effluent from the enzyme reactor such that the amount of more than one product formed in the enzyme reactor can be measured.

* * * * *

UNITED STATES PATENT AND TRADEMARK OFFICE
CERTIFICATE OF CORRECTION

PATENT NO. : 4,865,984
DATED : September 12, 1989
INVENTOR(S) : Nemerson et al.

It is certified that error appears in the above-identified patent and that said Letters Patent is hereby corrected as shown below:

Column 8, line 25, "110" should read --1-10--.

Column 8, line 65, before "the tubes" insert --The streams exiting--.

Signed and Sealed this

Fourteenth Day of August, 1990

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,865,984

DATED : September 12, 1989

INVENTOR(S) : Nemerson et al.

It is certified that error appears in the above-identified patent and that said Letters Patent is hereby corrected as shown below:

In column 1, line 5, before the words "BACKGROUND OF THE INVENTION" insert

--This invention was made with government support under grant #HL-29019 awarded by the National Institutes of Health. The government has certain rights in the invention.--

Signed and Sealed this

Thirteenth Day of October, 1992

Attest:

DOUGLAS B. COMER

*Attesting Officer*     *Acting Commissioner of Patents and Trademarks*